US010194658B2

(12) United States Patent
Sheth et al.

(10) Patent No.: US 10,194,658 B2
(45) Date of Patent: Feb. 5, 2019

(54) HIGH CONCENTRATION LOW VOC LIQUID GIBBERELLIN

(71) Applicants: Ritesh Sheth, Friendswood, TX (US); Christopher George, Houston, TX (US); Jerry Stoller, Houston, TX (US)

(72) Inventors: Ritesh Sheth, Friendswood, TX (US); Christopher George, Houston, TX (US); Jerry Stoller, Houston, TX (US)

(73) Assignee: Stoller Enterprises, Inc., Houston, TX (US)

( * ) Notice: Subject to any disclaimer, the term of this patent is extended or adjusted under 35 U.S.C. 154(b) by 1 day.

(21) Appl. No.: 15/210,087

(22) Filed: Jul. 14, 2016

(65) Prior Publication Data

US 2017/0013836 A1 Jan. 19, 2017

Related U.S. Application Data

(60) Provisional application No. 62/192,519, filed on Jul. 14, 2015.

(51) Int. Cl.

| | |
|---|---|
| ***A01N 43/12*** | (2006.01) |
| ***A01N 25/02*** | (2006.01) |
| ***A01N 25/22*** | (2006.01) |
| ***A01N 45/00*** | (2006.01) |

(52) U.S. Cl.
CPC ............ *A01N 43/12* (2013.01); *A01N 25/02* (2013.01); *A01N 25/22* (2013.01); *A01N 45/00* (2013.01)

(58) Field of Classification Search
CPC ........ A01N 43/12; A01N 45/00; A01N 25/22; A01N 25/02
See application file for complete search history.

(56) References Cited

U.S. PATENT DOCUMENTS

| | | | | |
|---|---|---|---|---|
| 4,154,596 A * | 5/1979 | George | A01N 45/00 504/297 |
| 4,936,901 A | 6/1990 | Surgant, Sr. et al. | |
| 5,622,658 A | 4/1997 | Lloyd et al. | |
| 6,756,344 B2 * | 6/2004 | Killick | A01N 43/90 504/297 |
| 6,984,609 B2 | 1/2006 | Devisetty et al. | |
| 2005/0288188 A1 | 12/2005 | Volgas et al. | |
| 2006/0172890 A1 | 8/2006 | Datta et al. | |
| 2008/0039322 A1 | 2/2008 | Wang et al. | |
| 2010/0216641 A1 | 8/2010 | Wang et al. | |
| 2015/0173365 A1 | 6/2015 | Devisetty et al. | |
| 2016/0198714 A1 | 7/2016 | Stoller et al. | |

FOREIGN PATENT DOCUMENTS

| | | |
|---|---|---|
| EP | 0252897 | 1/1988 |

* cited by examiner

*Primary Examiner* — Sue X Liu
*Assistant Examiner* — Andriae M Holt
(74) *Attorney, Agent, or Firm* — Yancy IP Law, PLLC

(57) ABSTRACT

The invention relates generally to a liquid solution formulation including gibberellic acid ("$GA_3$"), gibberellin$_4$ ("$GA_4$"), gibberellin$_{4/7}$ ("$GA_{4/7}$"), or combinations thereof, and a low-volatile, organic solvent, and methods of their use. Specifically, the liquid solution formulations of the present invention are directed toward agricultural liquid solution formulations including at least one gibberellin and a low-volatile, organic solvent selected from polyethylene glycol, propylene glycol, and/or a non-polymeric glycol.

11 Claims, No Drawings

HIGH CONCENTRATION LOW VOC LIQUID GIBBERELLIN

CROSS-REFERENCE TO RELATED APPLICATION

This application claims the benefit, under 35 U.S.C. 119(e), of U.S. Provisional Application No. 62/192,519 filed Jul. 14, 2015, the contents of which are incorporated herein by reference.

BACKGROUND OF THE INVENTION

Field of the Invention

The present invention relates to gibberellic acid ("$GA_3$"), gibberellin$_4$ ("$GA_4$"), or gibberellin$_{4/7}$ ("$GA_{4/7}$") formulations containing low amounts of volatile organic chemicals ("VOCs") and methods of their use.

Description of Related Art

Gibberellins are a class of plant growth regulators which are diterpenoid acids. Gibberellins are commercially produced by fermentation of a natural fungus, Gibber ellafugikuroi. Gibberellins are marketed under various trade names and are commercially used on a variety of fruit orchards, vegetable crops, row crops, and ornamental crops. The predominantly used gibberellin is $GA_3$.

VOCs contribute to the formation of ground-level ozone, which is harmful to human health and vegetation when present at high enough concentrations. In some areas, VOCs may be defined as those compounds with a vapor pressure greater than 0.1 mm Hg at 20° C. CADPR (California Department of Pesticide Regulation) defines gibberellin formulations with greater than 25% emission potential, as determined by thermo gravimetric analysis ("TGA"), to be High-VOC products. TGA involves heating a pesticide sample in an environmentally controlled chamber while the rate of sample mass loss is measured. CADPR states that the emission potential of a pesticide formulation is determined by taking the mean of three replicate TGA measurements of the pesticide(s) and then subtracting the percent water and the exempt compounds from the measurement. The TGA process is well known by those of skill in the art.

Gibberellin solution formulations of the prior art are disadvantageous in several respects. The formulations are less concentrated due to low solubility of gibberellins, have limited storage stability, and/or contain unacceptable amounts of VOCs.

In order to overcome solubility issues, some formulations use solvents with amounts of VOCs that are not safe for the environment. For example, isopropyl alcohol and methyl alcohol offer severe disadvantages such as flammability and toxicity, which lead to restrictions in manufacturing, packaging, labeling, transportation, and warehousing of such solutions. Tetrahydrofurfuryl alcohol ("THFA") is considered corrosive to the eye and skin.

Moreover, the low solubility of $GA_3$, $GA_4$, and $GA_{4/7}$ in some solvents does not permit preparation of high potency solution formulations. These low strength solution formulations require larger packaging, more storage space, and higher associated transportation, warehousing, and container disposal costs. Due to very low solubility and undesirable hydrolysis, it has been especially difficult to formulate $GA_3$ in aqueous systems.

One way to overcome the solubility issues with $GA_3$, $GA_4$, and $GA_{4/7}$ is to prepare soluble powder formulations. These powder formulations dissolve readily when mixed with water and form true solutions. Once the solution is formed, no further mixing or agitation of the tank-mix is required.

Another way to overcome the solubility issues is to create a wettable powder. A wettable powder formulation is a dry, finely ground formulation. In this type of formulation, the active ingredient is combined with a finely ground dry carrier, usually a mineral clay, along with other ingredients that enhance the ability of the powder to be suspended in water. Upon mixing the wettable powder with water, a suspension is formed, which is then applied by a spray technique. Often the spray liquid must be continuously mixed to prevent settling of insoluble compositions.

However, wettable powders and soluble powder formulations tend to produce dust upon handling, such as when pouring, transferring or measuring them. This dust may pose health hazards. Further, powder formulations tend to wet poorly and also solubilize slowly upon addition to water. Powder formulations thus take longer times to wet, disperse and solubilize in the tank-mix. Formation of lumps or partially solubilized spray solutions will lead to uneven distribution of the plant growth regulator in the tank-mix with potential for reduced field performance. Sometimes, foam in the spray tank caused by spray tank adjuvants can also affect wetting and solubility of wettable and soluble powders. Wettable powder formulations will also leave undesirable insoluble residues both in the tank and on the sprayed foliage and fruit.

Another type of agricultural formulation is a tablet. Tablet formulations are pre-measured dosage delivery systems. They are useful in small areas, or for ornamental purposes. Tablet formulations may be effervescent, which dissolve in water over a period of two to ten minutes depending upon the type and size of the tablet. However, tablets generally deliver only between 0.1 to 1 gram of active ingredient per tablet. They are not ideal for large-scale field operations. Moreover, effervescent tablets are highly susceptible to humidity and may be slow to dissolve and are expensive.

Yet another type of agricultural formulation is a water-dispersible granule. Water-dispersible granules are also known as wettable granules or dry flowables. This type of formulation is similar to a wettable powder, except that the active ingredient is formulated as a dispersible granule. To prepare the water-dispersible granules for spray application, they are dispersed in water and form a suspension upon agitation. Many different water-dispersible granular formulations are known for agricultural chemicals.

Water-dispersible granules usually have no greater than eight percent moisture content, and form suspensions when added to aqueous solutions. The resulting suspension must be agitated for a period of time in order to fully disperse it. Agitation or by-pass recirculation of the tank-mix must also be maintained during application. The quality of water-dispersible granules is highly process- and active-ingredient-dependent; and can result in low yield recoveries, poor attrition resistance leading to dust potential, high manufacturing cost and poor dispersion. Generally, sprays of dissolved water-dispersible granular formulations leave undesirable insoluble residues on the treated foliage and fruit.

For $GA_3$, $GA_4$, and $GA_{4/7}$ formulations to be efficacious, the active ingredient must solubilize in tank-mixes prior to application. Otherwise, product efficacy will be severely affected. When water-dispersible granules are used, the grower often may not know when he has achieved the total solubility of the active ingredient in the spray solutions. In addition, water-dispersible granules can harden over time and thus result in poor dispersibility and solubility of the active ingredient. In addition, dust and caking may be problems with certain water-dispersible granules and powder formulations.

Currently, there is a strong market demand for high quality table grapes. One way to obtain grape berries of sufficient size is to thin the vines. There is a need for a consistent chemical thinning material that will improve berry cluster quality in order to save the costs of manually thinning each grape berry cluster. Concentrated, water-soluble, granular plant growth regulator formulations are known. However, some orchard growers would prefer solution formulations that are easier to apply.

Therefore, there is a need for environmentally safe, non-phytotoxic, efficacious, high strength gibberellin solution formulations. The improved formulations should overcome the toxicity, handling, storage, transportation, human exposure, and solubility issues encountered by prior art formulations. The formulations should also include low amounts of VOCs in order to be environmentally safe and be safer for growers to tank mix prior to application.

SUMMARY OF THE INVENTION

The present invention is an effective agricultural liquid solution formulation which has low levels of VOCs and, accordingly, is environmentally safe. The liquid solution formulation comprises at least one gibberellin and at least one low-volatile, organic solvent, wherein the formulation has a low level of volatile organic chemicals at a vapor pressure greater than 0.08 mm Hg at 20° C. or a volatile organic chemical (VOC) emission potential of ≤25%. "Low-volatile, organic solvents" are defined herein as those compounds with a vapor pressure greater than 0.08 mm Hg at 20° C., or alternatively, greater than 0.1 mm Hg at 20° C., or a volatile organic chemical (VOC) emission potential of ≤25%.

A first embodiment of the present invention is directed toward a liquid solution formulations including at least one gibberellin selected from the group consisting of $GA_3$, $GA_4$ and $GA_{4/7}$, at least one polyethylene glycol with a molecular weight from about 190 to 420, an optional non-aqueous co-solvent, an optional surfactant, and/or an optional minerals. Polyethylene glycol 200, also called PEG 200, is a low volatile organic liquid under the California regulations for low VOC's. It is a polyether compound with the structure: $H—(O—CH_2—CH_2)_n—OH$. PEGs are prepared by polymerization of ethylene oxide and are commercially available over a wide range of molecular weights up to 10,000,000 g/mol. The number following "polyethylene glycol", or "PEG", refers generally to the molecular weight. For example, PEG 200 has a range of molecular weights from 190 to 210, PEG 300 from 285 to 315, and PEG 400 from 380 to 420 g/mol. It is a clear, viscous liquid.

A second embodiment of the present invention is directed toward a liquid solution formulations comprising a gibberellin selected from the group consisting $GA_3$, $GA_4$ and $GA_{4/7}$ in propylene glycol. Propylene glycol, also called propane-1,2-diol, is an organic compound with the chemical formula $C_3H_8O_2$. The compound is sometimes called α-propylene glycol to distinguish it from the isomer propane-1,3-diol (β-propylene glycol). It is a viscous, colorless liquid which is nearly odorless but possesses a faintly sweet taste. Propylene glycol is a "low-volatile, organic solvent" within the meaning of the present invention.

A third embodiment of the present invention is directed toward a liquid solution formulations comprising at least one gibberellin selected from the group consisting of $GA_3$, $GA_4$ and $GA_{4/7}$ in non-polymeric ethylene glycols. Non-polymeric ethylene glycol mixtures may include, but are not limited to, triethylene glycol, tetraethylene glycol, and pentaethylene glycol. These non-polymeric ethylene glycols are considered "Low-volatile, organic solvent" within the meaning of the present invention.

The invention is also directed to methods for regulating plant growth comprising the step of treating a seed, fruit, soil or a plant with an effective amount of the liquid solution formulations of the present invention.

DETAILED DESCRIPTION OF THE INVENTION

The present invention is an effective agricultural liquid solution formulation which has low levels of VOCs and, accordingly, is environmentally safe. The liquid solution formulation comprises: a) at least one gibberellin; and b) at least one low-volatile, organic solvent. The gibberellin is selected from the group consisting of $GA_3$, $GA_4$, and $GA_{4/7}$. The low-volatile, organic solvent is selected from the group consisting of at least one polyethylene glycol with a molecular weight from about 190-420, propylene glycol, and at least one non-polymeric glycol. Optionally, the liquid solution formulation may include at least one non-aqueous co-solvent, at least one surfactant, and/or at least one mineral. The liquid formulation has a low level of volatile organic chemicals at a vapor pressure greater than 0.08 mm Hg at 20° C. or the liquid formulation has a volatile organic chemical (VOC) emission potential of ≤25%. The present liquid solution formulations are also storage stable and non-phytotoxic while being efficacious.

As provided herein, the liquid solution formulation is preferably non-aqueous. The term "non-aqueous", as used herein, is understood to include small amounts of water, preferably less than 5 wt. %, preferably less than 4 wt. %, preferably less than 3 wt. %, preferably less than 2 wt. %, preferably less than 1 wt. %, and preferably less than 0.5 wt. %. However, it is preferred that water is not intentionally added to the present formulation.

One embodiment of the present invention is directed to agricultural liquid solution formulations comprising: a) from about 0.001 to about 16 wt. % of at least one gibberellin selected from the group consisting of $GA_3$, $GA_4$, and $GA_{4/7}$, b) from about 55 to about 99.9 wt. % of at least one polyethylene glycol with a molecular weight from about 190-420; and c) 0-20 wt %. at least one non-aqueous co-solvent, d) 0-20 wt. % optional non-ionic or anionic surfactant, and e) optional mineral, wherein the liquid formulation has a low level of volatile organic chemicals at a vapor pressure greater than 0.08 mm Hg at 20° C. or said liquid formulation has a volatile organic chemical (VOC) emission potential of ≤25%, and wherein the percentages are percent by weight of the formulation. Preferably, this embodiment only includes the gibberellin $GA_3$. In another preferred alternative to this embodiment, the only polyethylene glycol present has a molecular weight from about 190-210. Alternatively, the formulation in this embodiment preferably includes $GA_3$ as the only gibberellin present, preferably in 4-15.5 wt. % $GA_3$, or 10.5-16 wt. % $GA_3$, or 12.5-15.8 wt. % $GA_3$.

Another embodiment of the present invention is directed to agricultural liquid solution formulations comprising: a) from about 10 to about 15 wt. % at least one gibberellin selected from the group consisting of $GA_3$, $GA_4$, and $GA_{4/7}$, b) from about 70 to about 84.5% of at least one polyethylene glycol with a molecular weight from about 190-420, c) 0-20 wt %. at least one non-aqueous co-solvent, and d) 0-20% non-ionic or anionic surfactant, and e) optional mineral, wherein the liquid formulation has a low level of volatile organic chemicals at a vapor pressure greater than 0.08 mm Hg at 20° C. or said liquid formulation has a volatile organic chemical (VOC) emission potential of ≤25%, and wherein the percentages are percent by weight of the formulation. Preferably, this embodiment only includes the gibberellin $GA_3$. In another preferred alternative to this embodiment, the only polyethylene glycol in the formulation has a molecular weight from about 190-210.

In yet another embodiment, the present invention is directed to an agricultural liquid solution formulations comprising: a) from about 0.1 to about 20 wt % at least one gibberellin selected from the group consisting of $GA_3$, $GA_4$, and $GA_{4/7}$, b) from about 40-80 wt % propylene glycol, c) from about 0 to 20 wt % optional non-aqueous co-solvent, d) from about 0-20 wt % optional non-ionic or anionic surfactant, and e) optional mineral, wherein the liquid formulation has a low level of volatile organic chemicals at a vapor pressure greater than 0.08 mm Hg at 20° C. or said liquid formulation has a volatile organic chemical (VOC) emission potential of ≤25%, and wherein the percentages are percent by weight of the formulation. The vapor pressure of propylene glycol classifies it as a low volatile organic compound (VOC) in some areas with a vapor pressure of 0.08 mm Hg at 20° C. Therefore, propylene glycol is considered "a low volatile organic compound" within the meaning of the present invention. Preferably, this embodiment only includes the gibberellin $GA_3$. Alternatively, the formulation in this embodiment preferably includes 4-20 wt. % $GA_3$, or 15-20 wt. % $GA_3$.

In yet another embodiment, the present invention is directed to an agricultural liquid solution formulations comprising: a) from about 0.001 to about 20 wt % at least one gibberellin selected from the group consisting of $GA_3$, $GA_4$, and $GA_{4/7}$, b) from about 51-99.9 wt % non-polymeric glycols, c) from about 0 to 20 wt % optional non-aqueous co-solvent, d) from about 0-20 wt % optional non-ionic or anionic surfactant, and e) optional mineral, wherein the liquid formulation has a low level of volatile organic chemicals at a vapor pressure greater than 0.08 mm Hg at 20° C. or said liquid formulation has a volatile organic chemical (VOC) emission potential of ≤25%, and wherein the percentages are percent by weight of the formulation. Preferably, this embodiment only includes the gibberellin $GA_3$. Alternatively, the formulation in this embodiment preferably includes only $GA_3$ as the gibberellin at 4-20 wt. % $GA_3$.

For each of the above-identified embodiments, the non-aqueous co-solvent is an organic solvent, including but not limited to polar and non-polar organic solvents. A polar solvent is defined as that which dissolves ionic and other polar solutes. Semi-polar solvents induce a certain degree of polarity in non-polar molecules. A measurement of polarity may be determined by its dielectric constant. Semi- and polar solvents defined in this invention are those solvents that have dielectric constants greater than 10 @ 20° C. For example, polar organic solvents may include, but are not limited to alcohols, dialkyl ketones, alkylene carbonates, alkyl esters, pyrollidones and aryl esters. Non-ionic or anionic surfactants are including, but not limited to the group consisting of carboxylates, sulfonates, natural oils, alkylamides, arylamides, alkylphenols, arylphenols, ethoxylated alcohols, polyoxygethylene, carboxylic esters, polyalkylglycol esters, anhydrosorbitols, glycol esters, carboxylic amides, monoalkanolamine, poloxyethylene fatty acid amides, polysorbates, cyclodextrins, sugar based, silicone based, polyalkylated alcohols, and alkylaryl ethoxylates.

It should be understood that the recitation of a range of values includes all of the specific values in between the highest and lowest value. For example, the recitation of "about 10.5 to about 15.5%" includes all of the values between 10.5 to about 15.5 such that either the upper or lower limits may include, but are not limited to 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, and 15.5. For example, the recitation of "about 0 to 20%" includes all of the values between 20 and 20 such that either the upper or lower limits may include, but are not limited to, 0, 1, 2, 3, 4, 5, 6, 7, 8, 9, 10, 11, 12, 13, 14, 15, 16, 17, 18, 19, and 20. For example, the recitation of "0.1 to about 10" includes all of the values between 0.1 and 5 such that either the upper or lower limits may include, but are not limited to, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, and 10.

The term mineral includes, but is not limited to, metal chlorides, metal sulfates, sodium or potassium salts of, and chelated metals. Specific examples include, but are not limited to metal chlorides, metal sulfates, EDTA chelated metals, and other suitable metal compounds.

In one embodiment, the invention is directed to methods of regulating plant growth comprising the step of treating a seed, fruit, soil or a plant with an effective amount of the formulations of the present invention. The formulation may be diluted with water and spray-applied.

Formulations of the present invention may be used on any plant in need of gibberellin treatment, for example, on: artichokes to accelerate maturity and increase yield; blueberries to improve fruit set and fruit size; bananas to stimulate plant growth and reduce effects of stress, or post-harvest for maintaining fruit quality; carrots to maintain foliage growth during periods of stress; celery to increase plant height and yield; cherries to increase fruit size, firmness and quality or to delay maturity for a more orderly harvest; citrus to increase fruit set and yield, to delay rind aging, reduce physiological disorders, or delay maturity for a more orderly harvest; collard greens to facilitate harvest, increase yield, and improve quality; cotton to promote early season growth and increase seedling vigor; and cucumbers to stimulate fruit set during periods of cool weather; pasture land used for animal grazing; and corn. The formulations can be used post harvest on bananas and citrus, etc. Formulations of the present invention could also be used on grapes, melons, pecans, peppers, pineapples, rice, rhubarb, spinach, stone fruits, strawberries, watercress and other plants in need of treatment.

The term "effective amount" means the amount of the formulation that will provide the desired effect on the plant that is being treated. The "effective amount" will vary depending on the formulation concentration, the type of plants(s) being treated, and the result desired, among other factors. Thus, it is not always possible to specify an exact "effective amount." However, an appropriate "effective amount" in any individual case may be determined by one of ordinary skill in the art.

Other plant growth regulators (PGRs) may be used in the present formulations to achieve stable and environmentally safe liquid solution formulations. The phrase "plant growth regulator" as used herein connotes a product which serves to modify the growth and the development of a treated plant to agricultural maturity without killing the plant. Such modification may result from the effect of the material on the physiological processes of the plant, or from the effect of said material on the morphology of the plant. These modifications may also result from any combination or sequence of physiological or morphological factors. Other plant growth regulators may be used such as, a cytokinin such as TDZ, Kinetin, or 6-benzyladenine, an auxin, an organic acid, an ethylene biosynthesis inhibitor, or a combination thereof Other components of the formulation may be included in nominal amounts that do not affect the storage stability or low VOC characteristics of the present formulations. Additional components include surface active agents, crystal growth inhibitors, stickers, spreaders, leaf penetrants, dispersants, systemic acquired resistance inducers, systemic acquired resistance inhibiters, anti-foaming agents, preservatives, pH regulators, cosolvents, humectants, dyes, UV protectants, vehicles, sequestrants or other components which facilitate production, storage stability, product handling and application.

It is also contemplated that the ready-to-mix composition materials of this invention may be used in combination with other active ingredients, such as herbicides, fungicides, insecticides, bactericides, nematicides, biochemical pesticides, plant produced pesticides (botanicals), safeners or plant nutrients. Applicant discovered that the use of propylene glycol as a solvent for pesticidal agents in dispersible concentrates can be stored at −18° C. for multiple years. Furthermore, the formulations are chemically and physically stable at elevated temperatures and freeze thaw cycles.

As used herein, the term "herbicide" broadly refers to compounds or compositions that are used as herbicides, as well as herbicide safeners and algicides. Herbicides may include, but are not limited to, 1,2,4-triazinones, 1,3,5-triazines, alkanamides (acetamides), anilides, aryloxyalkanoic acids, aryloxyphenoxypropionates, benzamides, benzamides (L), benzenedicarboxylic acids, benzofurans, benzoic acids (auxins), benzonitriles, benzothiadiazinones, benzothiazolones, carbamates (DHP), carbamates, chloroacetamides, cyclohexanedione oximes, dinitroanilines, dinitrophenols, diphenyl ethers, diphenyl ethers (cbi), glycine derivatives, halogenated alkanoic acids, hydroxybenzonitriles, imidazolinones, isoxazoles, isoxazolidinones, N-phenylphthalimides, organoarsenics, oxadiazoles, oxazolidinediones, oxyacetamides, phenoxycarboxylic acids, phenyl carbamate herbicides, phenylpyrazole herbicides, phenylpyridazines, phosphinic acids, phos-phorodithioates, phthalamates, pyrazole herbicides, pyridazines, pyridazinones (PDS), pyridazinones (PSII), pyridines, pyridinecarboxamides, pyridinecarboxylic acids, pyrimidindiones, pyrimidines, pyrimidinyl-oxybenzoics, pyrimidinyloxybenzoic analogs, quinolinecarboxylic acids, BI class IV: thiocarbamate, semi-carbazones, sulfonylaminocarbonyl-triazolinones, sulfonylureas, tetrazolinones, thiadiazoles, thiocarbamates, triazoles, triazolinones, triazolopyrimidines, triketones, uracils, and ureas. Suitable herbicides include 2,3,6-TBA, 2,4,5-T, 2,4-D, 2,4-D-2-ethylhexyl, 2,4-DB, 2,4-D-dimethylammonium, 2,4-D-isopropyl, 2,4-D-isopropyl, 2,4-D-trolamine (2,4-D-triethanolamine), ACD 10614; ACD 10435, acetochlor, acifluorfen, acifluorfen-sodium, aclonifen, acrolein, AD 67, alachlor, alloxydim-sodium, ametryn, amicarbazone, amidosulfuron, amitrole, ammonium sulfamate, anilofos, asulam, atraton, atrazine, azafenidin, azimsulfuron, aziprotryne, barban, beflubutamid, benazolin, benazolin-ethyl, benfluralin, benfuresate, benoxacor, bensulfuron-methyl, bensulide, bentazone, benzobicyclon, benzofenap, benzoylprop, enzoylprop-ethyl, bifenox, bilanafos-sodium, bispyribac-sodium, borax, bromacil, bromobutide, bromofenoxim, bromoxynil, bromoxynil octanoate, bromoxynil-potassium, brompyrazon, butachlor, butafenacil, butenachlor, buthidazole, butralin, butroxydim, buturon, cafenstrole, calcium cyan-amide, carbetamide, carfentrazone-ethyl, chlomethoxyfen, chloramben, chlorbromuron, chlorbufam, chlorfenac, chlorfenac-sodium, chlorfenprop, chlorfenprop-methyl, chlorfenprop, chlorfenprop-ethyl, chlorflurenol-methyl, chloridazon, chlorimuron-ethyl, chlornitrofen, chloroacetic acid, chloro-toluron, chloroxuron, chlorpropham, chlorsulfuron, chlorthal-dimethyl, chlorthiamid, cinidon-ethyl, cinosulfuron, clodinafop-propargyl, clofop, clofop-isobutyl, clomazone, clomeprop, clopyralid, cloquintocet-mexyl, cloransulam-methyl, credazine, cumyluron, cyanamide, cyanazine, cyclosulfamuron, cycloxydim, cycluron, cyhalofop-butyl, cyometrinil, daimuron, dazomet, desmedipham, desmetryn, di-allate, dicamba, dichlobenil, dichlormid, dichlorprop, dichlorprop-isoctyl, dichlorprop-P, diclofop, diclofop-methyl, diclosulam, diethatyl-ethyl; diethatyl, difenoxuron, difenzoquat metilsulfate, diflufenican, diflufenzopyr, dikegulac, dikegulac-sodium, dimefuron, dimepiperate, dimethachlor, dimethametryn, dimethipin, dimethylarsinic acid, dinitramine dinoseb, dinoseb acetate, dinoterb, diphenamid, dipropetryn, disul, disul-sodium, dithiopyr, diuron, DNOC, DSMA, eglinazine-ethyl, eglinazine, EL 177, endothal, ethalfluralin, ethametsulfuron-methyl, ethidimuron, ethofumesate, ethoxysulfuron, etobenzanid, fenchlorazole-ethyl, fenclorim, fenoprop, fenoprop-butotyl, fenoxaprop-ethyl, fenoxaprop, fenoxaprop-P, fenoxaprop-P-ethyl, fenthiaprop; fenthiaprop-ethyl, fentrazamide, fenuron, flamprop-methyl, flamprop-isopropyl, flamprop, flamprop-M-isopropyl, flamprop-M-methyl, flazasulfuron, florasulam, fluazifop-butyl, fluazifop-P, fluazifop-P-butyl, fluazolate, flucarbazone-sodium, fluchloralin, flufenacet, flumetsulam, flumiclorac-pentyl, flumioxazin, flumipropyn, fluometuron, fluorodifen, fluoroglycofen-ethyl, fluothiuron, flupoxam, flupropanate-sodium, flupyr-sulfuron-methyl-sodium, flurazole, flurenol-butyl, fluridone, flurochloridone, fluroxypyr, fluroxypyr-meptyl, flurtamone, fluthiacet-methyl, fomesafen, foramsulfuron, fosamine-ammonium, furilazole, glufosinate-ammonium, glyphosate, glyphosate-ammonium, glyphosate-isopropylammonium, glyphosate-sodium, glyphosate-trimesium, halosulfuron-methyl, haloxyfop, haloxyfop-etotyl, haloxyfop-P, hexaflurate, hexazinone, imazamethabenz-methyl, imazamox, imazapic, imazapyr, imazapyr-isopropylammonium, imazaquin, imazethapyr, imazosulfuron, indanofan, iodosulfuron-methyl-sodium, ioxynil, ioxynil octanoate, ioxynil-sodium, isocarbamid, isocil, isomethiozin, isonoruron, isoproturon, isouron, isoxaben, isoxaflutole, isoxapyrifop, karbutilate, lactofen, lenacil, linuron, LS830556, maleic hydrazide, MCPA, MCPA-thioethyl, MCPB, MCPB-ethyl, mecoprop, mecoprop-P, medinoterb acetate, medinoterb, mefenacet, mefenpyr-diethyl, mefluidide, mesosulfuron-methyl, mesotrione, metamifop, metamitron, metazachlor, methabenzthiazuron, methazole, methiuron, methoprotryne, methoxyphenone, methyl isothiocyanate, methylarsonic acid, methyldymron, metobenzuron, metobromuron, metolachlor, metosulam, metoxuron, metribuzin, metsulfuron-, ethyl, MK-616, monalide, monolinuron, monuron, monuron-TCA, MSMA, naphthalic anhydride, naproanilide, napropamide, naptalam, NC-330, neburon, nicosulfuron, nitralin, nitrofen, nonanoic acid, norflurazon, oleic acid (fatty acids), orbencarb, oryzalin, oxabetrinil, oxadiargyl, oxadiazon, oxasulfuron, oxaziclomefone, oxyfluorfen, pendimethalin, penoxsulam, pentachloro-phenol, pentanochlor, pentoxazone, perfluidone, pethoxamid, phen-isopham, phenmedipham, phenylmercury acetate, picolinafen, primisulfuron-methyl, prodiamine, profluralin, proglinazine-ethyl, proglinazine, prometon, prometryn, propachlor, propanil, propaquizafop, propazine, propham, propisochlor, propoxycarbazone-sodium, propyzamide, prosulfuron, pyraflufen-ethyl, pyrazolynate, pyrazosulfuron-ethyl, pyrazoxyfen, pyribenzoxim, pyributicarb, pyridate, pyriftalid, pyriminobac-methyl, pyrithiobac-sodium, quinclorac, quinmerac, quinoclamine, quizalofop-ethyl, quizalofop-P-ethyl, quizalofop-P-tefuryl, rimsulfuron, sebuthylazine, secbumeton, siduron, simazine, simetryn, S-metolachlor, SMY 1500, sodium chlorate, sulcotrione, sulfentrazone, sulfometuron-methyl, sulfosulfuron, tebuthiuron, tepraloxydim, terbacil, terbumeton, terbuthylazine, terbutryn, thenylchlor, thiazafluron, thiazopyr, thidiazimin, thifensulfuron-methyl, thiobencarb, 1-dichloroacetylazepane, tralkoxydim, tri-allat, triasulfuron, tribenuron-methyl, trichloroacetic acid, triclopyr, tridiphane, trietazine, trifloxysulfuron-sodium, trifluralin, and triflusulfuron-methyl.

Fungicides may include, but are not limited to, amino acid amide carbamates, anilinopyrimidines, antibiotics, aromatic hydrocarbons, heteroaromatics, chloro/nitrophenyls, benzamides (F), benzenesulfonamides, benzimidazoles, benzimidazole precursors, benzotriazines, carboxamides, cinnamic acids, cyanoacetamide oximes, dicarboximides, dithiolanes, DMI: imidazoles, DMI: piperazines, DMI: pyrimidines, DMI: triazoles, enopyranuronic acid antibiotics, heteroaromatic hydroxyanilides, MBI: dehydratases, MBI: reductases, morpholine: morpholines, morpholine: spiroketalamines, multi-site: chloronitriles, multi-site: dimethyldithiocarbamates, multi-site: guanidines, multi-site: inorganics, multi-site: phthalimides, multi-site: quinones, multi-site: sulfamides, N-phenyl carbamate fungicides, organotin fungicides, phenylamide: acylalanines, phenylamide: butyrolactones, phenylamide: oxazolidinones, phenylpyrroles, phenylurea fungicides, phosphonates, phosphorothiolates, pyridazinone fungicides, pyrimidinamines, pyrimidinols, QiI, quinolines, SBI class IV: thiocarbamates, strobilurin analog: dihydrodioxazines, strobilurin type: imidazolinones, strobilurin type: methoxyacrylates, strobilurin type: ethoxycarbamates, strobilurin type: oxazolidinediones, strobilurin type: oximinoacetamides, strobilurin type: oximinoacetates, thiazolecarboxamides, thiocarbamate fungicides, and thiophenecarboxamides. Suitable fungicides include 1,2-dichloro-propane, 2-methoxyethylmercury chloride, 2-phenylphenol, 8-hydroxy-quinoline sulfate, ampropylfos, anilazine, azaconazole, azoxystrobin, benalaxyl, benodanil, benomyl, benquinox, benthiavalicarb-isopropyl, binapacryl, biphenyl, bis(tributyltin) oxide, bitertanol, blasticidin-S, borax, boscalid, bromuconazole, bupirimate, buthiobate, captafol, captan, carbendazim, carboxin, carpropamid, CGA 80 000, chinomethionat, chlobenthiazone, chloraniformethan, chloroneb, chlorothalonil, chlozolinate, climbazole, copper oxychloride, copper sulfate, copper sulfate (tribasic), cuprous oxide, cyazofamid, cyflufenamid, cymoxanil, cyproconazole, cyprodinil, cyprofuram, dazomet, dichlofluanid, dichlone, dichlorophen, diclobutrazol, diclocymet, diclomezine, dicloran, diethofencarb, difenoconazole, difenzoquat metilsulfate, diflumetorim, dimethirimol, dimethomorph, dimoxystrobin, diniconazole, dinobuton, dinocap, diphenylamine, ditalimfos, dithianon, dodemorph, dodemorph acetate, dodine, drazoxolon, edifenphos, epoxiconazole, etaconazole, etem, ethaboxam, ethirimol, etridiazole, famoxadone, fenamidone, fenarimol, fenbuconazole, fenfuram, fenhexamid, fenitropan, fenoxanil, fenpiclonil, fenpropimorph, fentin acetate, fentin hydroxide, ferimzone, fluazinam, fludioxonil, flumorph, fluoroimide, fluotrimazole, fluoxastrobin, fluquinconazole, flusilazole, flusulfamide, flutolanil, flutriafol, folpet, fosetyl-aluminum, fuberidazole, furalaxyl, furametpyr, furconazole-cis, furmecyclox, glyodin, griseofulvin, halacrinate, hexachlorobenzene, hexaconazole, hymexazol, imazalil, imibenconazole, iminoctadine triacetate, iminoctadine tris(albesilate), ipconazole, iprodione, iprovalicarb, isoprothiolane, kasugamycin hydrochloride hydrate, kresoxim-methyl, mebenil, mepanipyrim, mepronil, mercuric chloride, metalaxyl, metalaxyl-M, metconazole, methasulfocarb, methfuroxam, methyl iodide, methyl isothiocyanate, metominostrobin, metsulfovax, mildiomycin, myclobutanil, myclozolin, natamycin, nitrothal-isopropyl, nuarimol, ofurace, oleic acid, fatty acids), oxabetrinil, oxadixyl, oxpoconazole fumarate, oxycarboxin, penconazole, pencycuron, pentachlorophenol, phenylmercury acetate, phenylmercury dimethyldithiocarbamate, phenylmercury nitrate, phosphonic acid, phthalide, picoxystrobin, polyoxin B, polyoxorim, potassium bicarbonate, potassium hydroxyquinoline sulfate, prochloraz, procymidone, propamocarb hydrochloride, propiconazole, proquinazid, prothiocarb; prothiocarb hydrochloride, prothioconazole, pyracarbolid, pyraclostrobin, pyrazophos, pyributicarb, pyrimethanil, pyroquilon, quinoclamine, quinoxyfen, quintozene, silthiofam, simeconazole, sodium bicarbonate, spiroxamine, SSF-109, sulfur, tebuconazole, tecnazene, tetraconazole, thiabendazole, thicyofen, thifluzamide, thiophanate, thiophanate-methyl, thiram, tiadinil, tolclofos-methyl, tolylfluanid, triadimefon, triadimenol, triamiphos, triazoxide, trichlamide, tricyclazole, trifloxystrobin, triflumizole, triforine, triticonazole, urbacid, validamycin, vinclozolin, zarilamid, ziram, and zoxamide.

Bactericides may include, but are not limited to, bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulfate and other copperpreparations.

Insecticides, acaricides and nematicides may include, but are not limited to, abamectin, ABG-9008, acephate, acequinocyl, acetamiprid, acetoprole, acrinathrin, AKD-1022, AKD-3059, AKD-3088, alanycarb, aldicarb, aldoxycarb, allethrin, alpha-cypermethrin (alphamethrin), amidoflumet, aminocarb, amitraz, avermectin, AZ-60541, azadirachtin, azamethiphos, azinphos-methyl, azinphos-ethyl, azocyclotin, *Bacillus firmus, Bacillus popilliae, Bacillus sphaericus, Bacillus subtilis, Bacillus thuringiensis, Bacillus thuringiensis* strain EG-2348, *Bacillus thuringiensis* strain GC-91, *Bacillus thuringiensis* strain NCTC-11821, *Bacillus thuringiensis israelensis*, baculoviruses, *Beauveria bassiana, Beauveria tenella*, benclothiaz, bendiocarb, benfuracarb, bensultap, benzoximate, beta-cyfluthrin, beta-cypermethrin, bifenazate, bifenthrin, binapacryl, bioallethrin, bioallethrin-5-cyclopentyl isomer, bioethanomethrin, biopermethrin, bioresmethrin, bistrifluoron, BPMC, brofenprox, bromophos-ethyl, bromopropylate, bromfenvinfos (-methyl), BTG-504, BTG-505, bufencarb, buprofezin, butathiofos, butocarboxim, butoxycarboxim, butylpyridaben, cadusafos, camphechlor, carbaryl, carbofuran, carbophenothion, carbosulfan, cartap, CGA-50439, chinomethionat, chlorantraniliprole, chlordane, chlordimeform, chloethocarb, chlorethoxyfos, chlorfenapyr, chlorfenvinphos, chlorfluazuron, chlormephos, chlorobenzilate, chloropicrin, chlorproxyfen, chlorpyrifos-methyl, chlorpyrifos (-ethyl), chlovaporthrin, chromafenozide, cis-cypermethrin, cisresmethrin, cis-permethrin, clocythrin, cloethocarb, clofentezine, clothianidin, clothiazoben, codlemone, coumaphos, cyanofenphos, cyanophos, cyantraniliprole, cycloprene, cycloprothrin, cyfluthrin, cyflumetofen, cyhalothrin, cyhexatin, cypermethrin, cyphenothrin (1R-trans-isomer), cyromazine, DDT, deltamethrin, demeton-5-methyl, demeton-5-methylsulfone, diafenthiuron, dialifos, diazinon, dichlofenthion, dichlorvos, dicofol, dicrotophos, dicyclanil, diflubenzuron, dimefluthrin, dimethoate, dimethylvinphos, dinobuton, dinocap, dinotefuran, diofenolan, disulfoton, docusat-sodium, dofenapyn, DOWCO-439, eflusilanate, emamectin, emamectin-benzoate, empenthrin (1R-isomer), endosulfan, *Entomopthora* spp., EPN, esfenvalerate, ethiofencarb, ethion, ethiprole, ethoprophos, etofenprox, etoxazole, etrimfos, famphur, fenamiphos, fenazaquin, fenbutatin oxide, fenfluthrin, fenitrothion, fenobucarb, fenothiocarb, fenoxacrim, fenoxycarb, fenpropathrin, fenpyrad, fenpyrithrin, fenpyroximate, fensulfothion, fenthion, fentrifanil, fenvalerate, fipronil, flonicamid, fluacrypyrim, fluazuron, flubendiamide, flubenzimine, flubrocythrinate, flucycloxuron, flucythrinate, flufenerim, flufenoxuron, flufenprox, flumethrin, flupyrazofos, flutenzin (flufenzine), fluvalinate, fonofos, formetanate, formothion, fosmethilan, fosthiazate, fubfenprox (fluproxyfen), furathiocarb, gamma-cyhalothrin, gamma-HCH, gossyplure, grandlure, granulosis viruses, halfenprox, halofenozide, HCH, HCN-801, heptenophos, hexaflumuron, hexythiazox, hydramethylnone, hydroprene, IKA-2002, imidacloprid, imiprothrin, indoxacarb, iodofenphos, iprobenfos, isazofos, isofenphos, isoprocarb, isoxathion, ivermectin, japonilure, kadethrin, nuclear polyhedrosis viruses, kinoprene, lambda-cyhalothrin, lindane, lufenuron, malathion, mecarbam, mesulfenfos, metaldehyde, metam-sodium, methacrifos, methamidophos, Metharhizium anisopliae, Metharhizium flavoviride, methidathion, methiocarb, methomyl, methoprene, methoxychlor, methoxyfenozide, metofluthrin, metolcarb, metoxadiazone, mevinphos, milbemectin, milbemycin, MKI-245, MON-45700, monocrotophos, moxidectin, MTI-800, naled, NC-104, NC-170, NC-184, NC-194, NC-196, niclosamide, nicotine, nitenpyram, nithiazine, NNI-0001, NNI-0101, NNI-0250, NNI-9768, novaluron, noviflumuron, OK-5101, OK-5201, OK-9601, OK-9602, OK-9701, OK-9802, omethoate, oxamyl, oxydemeton-methyl, *Paecilomyces fumosoroseus*, parathion-methyl, parathion (-ethyl), permethrin (cis-, trans-), petroleum, PH-6045, phenothrin (1R-trans isomer), phenthoate, phorate, phosalone, phosmet, phosphamidon, phosphocarb, phoxim, piperonyl butoxide, pirimicarb, pirimiphos-methyl, pirimiphos-ethyl, potassium oleate, prallethrin, profenofos, profluthrin, promecarb, propaphos, propargite, propetamphos, propoxur, prothiofos, prothoate, protrifenbute, pymetrozine, pyraclofos, pyrafluprole, pyresmethrin, pyrethrum, pyridaben, pyridalyl, pyridaphenthion, pyridathion, pyrimidifen, pyriprole, pyriproxyfen, quinalphos, resmethrin, RH-5849, ribavirin, RU-12457, RU-15525, rynaxapyr, S-421, S-1833, salithion, sebufos, SI-0009, silafluofen, spinosad, spirodiclofen, spiromesifen, sulfluramid, sulfotep, sulprofos, SZI-121, tau-fluvalinate, tebufenozide, tebufenpyrad, tebupirimfos, teflubenzuron, tefluthrin, temephos, temivinphos, terbam, terbufos, tetrachlorvinphos, tetradifon, tetramethrin, tetramethrin (1R-isomer), tetrasul, theta-cypermethrin, thiacloprid, thiamethoxam, thiapronil, thiatriphos, thiocyclam hydrogenoxalate, thiodicarb, thiofanox, thiometon, thiosultap-sodium, thuringiensin, tolfenpyrad, tralocythrin, tralomethrin, transfluthrin, triarathene, triazamate, triazophos, triazuron, trichlophenidine, trichlorfon, triflumuron, trimethacarb, vamidothion, vaniliprole, verbutin, *Verticillium lecanii*, WL-108477, WL-40027, y1-5201, y1-5301, y1-5302, XMC, xylylcarb, ZA-3274, zeta-cypermethrin, zolaprofos, ZXI-8901, the compound 3-methylphenyl propylcarbamate (Tsumacide Z), the compound 3-(5-chloro-3-pyridinyl)-8-(2,2,2-trifluoroethyl)-8-azabicyclo[3-.2.1]octane-3-carbonitrile (CAS-Reg. No. 185982-80-3) and the corresponding 3-endo-isomer (CAS-Reg. No. 185984-60-5) (cf. WO-96/37494, WO-98/25923), and also preparations which comprise insecticidally active plant extracts, nematodes, fungi or viruses.

As used herein, all numerical values relating to amounts, weight percentages and the like are defined as "about" or "approximately" each particular value, namely, plus or minus 10% (+−10%). For example, the phrase "at least 5% by weight" is to be understood as "at least 4.5% to 5.5% by weight." Therefore, amounts within 10% of the claimed values are encompassed by the scope of the claims. The percentages of the components in the formulations are listed by weight percentage.

The disclosed embodiments are simply exemplary embodiments of the inventive concepts disclosed herein and should not be considered as limiting, unless the claims expressly state otherwise.

EXAMPLES

Preparation of Low VOC Formulations

Before preparing the formulations, the amount of the components must be calculated (see tables below). Applicants used $GA_3$, $GA_4$, and $GA_{4/7}$ in the form of Technical Grade Active Ingredient ("TGAI") when preparing formulations of the present invention. The percent $GA_3$, $GA_4$, and $GA_{4/7}$ in the technical grade typically ranged between 89% w/w to 95% w/w. Variations in the activity of $GA_3$, $GA_4$, and $GA_{4/7}$ in the TGAI should be accounted for by decreasing or increasing the amount of diluent in producing the desired percent of $GA_3$, $GA_4$, and/or $GA_{4/7}$ formulation. This is standard practice within the guidelines of US Environmental Protection Agency per 40 C.F.R. § 158.1.

General Method of Making

The non-aqueous solution is generally produced by dissolving gibberellic acid in organic solvent and mixing at a temperature preferably below 120° C., and most preferably below 100° C. It is believed that heating gibberellic acid in the polar and/or semi-polar organic solvent up to 100° C. will not significantly degrade the plant growth regulator. Table 1 below summarizes the examples of $GA_3$ in low-VOC solvent systems. Below the table are further detailed descriptions of creating the formulations.

TABLE 1

Summary of Examples

| Ex. | % GA3 | % Solvent | Solvent | % Co-Solvent | Co-Solvent | % Surfactant | % Mineral |
|---|---|---|---|---|---|---|---|
| 1 | 15 | 84.5 | PEG 200 | 0 | NA | 0.5 | 0 |
| 2 | 15 | 69.5 | PEG 200 | 15 | Ethanol | 0.5 | 0 |
| 3 | 10 | 74.9 | PEG 200 | 15 | Propylene Glycol | 0 | 0.1 |
| 4 | 20 | 69.5 | Propylene Glycol | 0 | NA | 0.5 | 0 |
| 5 | 15.5 | 83.9 | Propylene Glycol | 0 | NA | 0.5 | 0.1 |
| 6 | 10.5 | 89 | Molex G-612 | 0 | NA | 0.5 | 0 |
| 7 | 10.5 | 74.5 | Molex G-612 | 15 | Propylene Glycol | 0 | 0 |

Example 1

Preparation of a Low VOC 15% Gibberellic Acid Formulation

TABLE 2

| Raw Material | % wt/wt | g/batch |
|---|---|---|
| PEG 200 | 84.5 | 845 |
| $GA_3$ TGAI, 90% purity | 15 | 15 |
| Surfactant | 0.50 | 5.00 |
| Total | 100 | 1000.0 |

As shown in Table 2, 845 grams of PEG 200 charged in a 2-liter glass beaker. The surfactant and $GA_3$ were added while mixing and heating (temperature less than 100° C.). The heat source was turned off while stirring continued. The mixing was continued for 60 minutes and the formulation was allowed to cool prior to packaging.

Example 3

Preparation of a Low VOC 15% Gibberellic Acid Formulation

TABLE 3

| Raw Material | % wt/wt | g/batch |
|---|---|---|
| PEG 200 | 70 | 730 |
| Hexanol | 15 | 150 |
| $GA_3$ TGAI, 90% purity | 12 | 120 |
| | 100 | 1000.0 |

As shown in Table 3, 730 grams of PEG 200 was charged in a 2-liter glass beaker and heated. The hexanol, surfactant, and $GA_3$ were charged and allowed to mix while heating (temperature less than 100° C.). The heat source was turned off while stirring continued. The mixing was continued for 60 minutes and the formulation was allowed to cool prior to packaging.

Example 4

Preparation of a Low VOC 15% Gibberellic Acid Formulation

TABLE 4

| Raw Material | % wt/wt | g/batch |
|---|---|---|
| PEG 200 | 74.9 | 749 |
| Propylene Glycol | 15 | 150 |
| $GA_3$ TGAI, 90% purity | 10 | 100 |
| Mixrite Zinc | 0.10 | 1.00 |
| | 100 | 1000.0 |

As shown in Table 4, 749 grams of PEG 200 was charged in a 2-liter glass beaker and heated. The propylene glycol, $GA_3$, and Mixrite Zinc were charged and allowed to mix for 15 minutes while heating (temperature less than 100° C.). The heat source was turned off while stirring continued. The mixing was continued for 60 minutes and the formulation was allowed to cool prior to packaging.

Example 5

Preparation of a Low VOC 15% Gibberellic Acid Formulation

TABLE 5

| Raw Material | % wt/wt | g/batch |
|---|---|---|
| Propylene Glycol | 69.5 | 695 |
| $GA_3$ TGAI, 90% purity | 20 | 200 |
| Surfactant | 0.50 | 5.00 |
| | 100 | 1000.0 |

As shown in Table 5, 695 grams of propylene glycol was charged in a 2-liter glass beaker. The surfactant and $GA_3$ were added while mixing and heating for 15 minutes (temperature less than 100° C.). The heat source was turned off while stirring continued. The mixing was continued for 60 minutes and the formulation was allowed to cool prior to packaging. A clear solution was obtained which contained 20% wt/wt $GA_3$.

Example 6

Preparation of a Low VOC 15% Gibberellic Acid Formulation

TABLE 6

| Raw Material | % wt/wt | g/batch |
|---|---|---|
| Propylene Glycol | 83.9 | 839 |
| Mixrite Zinc | 0.1 | 1 |
| $GA_3$ TGAI, 90% purity | 15.5 | 155 |
| Surfactant | 0.50 | 5.00 |
| | 100 | 1000.0 |

As shown in Table 6, 835 grams of propylene glycol was charged in a 2-liter glass beaker. The surfactant, Mixrite Zinc, and $GA_3$ were added while mixing and heating for 15 minutes (temperature less than 100° C.). Mixrite Zinc was added at 85° C. and the heat source was turned off while stirring continued. The mixing was continued for 60 minutes and the formulation was allowed to cool prior to packaging.

Example 7

Preparation of a Low VOC 10.5% Gibberellic Acid Formulation

TABLE 7

| Raw Material | % wt/wt | g/batch |
|---|---|---|
| Molex G-612 | 89 | 890 |
| $GA_3$ TGAI, 90% purity | 10.5 | 105 |
| Surfactant | 0.50 | 5.00 |
| | 100 | 1000.0 |

As shown in Table 7, 835 grams of Molex G-612 (non-polymeric higher glycol mixture) was charged in a 2-liter glass beaker. The surfactant and $GA_3$ were added while mixing and heating for 15 minutes (temperature less than 100° C.). The mixing was continued for 120 minutes and the formulation was allowed to cool prior to packaging. A clear solution was obtained which contained 10.5% wt/wt $GA_3$.

Example 8

Preparation of a Low VOC 10.5% Gibberellic Acid Formulation

TABLE 8

| Raw Material | % wt/wt | g/batch |
|---|---|---|
| Molex G-612 | 74.5 | 745 |
| $GA_3$ TGAI, 90% purity | 10.5 | 105 |
| Propylene Glycol | 15 | 150 |
| | 100 | 1000.0 |

As shown in Table 8 grams of Molex G-612 (non-polymeric higher glycol mixture) was charged in a 2-liter glass beaker. The propylene glycol and $GA_3$ were added while mixing and heating for 15 minutes (temperature less than 100° C.). The mixing was continued for 120 minutes and the formulation was allowed to cool prior to packaging. A clear solution was obtained which contained 10.5% wt/wt $GA_3$.

Volatile Organic Measurement

To calculate VOC measurements, the method "Estimation of Volatile Emission Potential of Pesticides by Thermogravimetry" from the California Department of Agriculture was used. This method utilizes thermogravimetric analysis (TGA) to determine VOC. Samples were heated in a controlled vessel and heated isothermally until the rate of sample mass loss drops below a defined threshold. The samples are run in replicates of three and the following equation is used to calculate VOC: Emission Potential (EP)=mean (% TGA sample mass loss)−(product % water)−(product % exempt compounds). Table 9 summarizes VOC examples. The emission potential (VOC rating/volatility) in the table below was determined by the sample mass loss in a computer-controlled oven chamber (TGA) using a recording microbalance to determine the endpoint. The present formulation has a VOC rating ≤25, which equates to a volatile organic chemical (VOC) emission potential of ≤25%.

TABLE 9

VOC Results Summary

| Example | % GA3 | % PEG 200 | % Co-Solvent | Co-Solvent | VOC Rating (Volatility) |
|---|---|---|---|---|---|
| 8 | 15.5 | 69.5 | 15 | Isopropanol | 10.4 |
| 9 | 15.5 | 69.5 | 15 | Ethanol | 6.4 |
| 10 | 15 | 70 | 15 | Hexanol | 18 |
| 11 | 15 | 70 | 15 | 3-Hydroxybutyrate | 17.7 |
| 12 | 15.5 | 69.5 | 15 | 3-Butyl Lactate | 17 |
| 13 | 15.5 | 69.5 | 15 | 2-Ethylhexyl lactate | 15.2 |
| 14 | 15.5 | 69.5 | 15 | Propylene glycol | 20.5 |
| 15 | 15.5 | 64.5 | 20 | Propylene glycol | 25 |

We claim:

1. A non-aqueous liquid solution formulation comprising:

a) 10.5 to about 20 wt. % of at least one gibberellin selected from the group consisting of $GA_3$, $GA_4$, and $GA_{4/7}$ as the only gibberellins present in said non-aqueous liquid solution, b) 69.5 to 74.9 wt. % of a low-volatile, organic solvent selected from the group consisting of at least one polyethylene glycol with a molecular weight from about 190-420;

c) 10 to about 20 wt. % of at least one non-aqueous co-solvent selected from a group of polar solvents;

d) 0 to about 5 wt. % at least one surfactant, and e) optionally, at least one mineral, wherein said liquid solution formulation has a low level of volatile organic chemicals such that the vapor pressure of said liquid solution formulation is greater than 0.08 mm Hg at 20° C. or said liquid solution formulation has a volatile organic chemical (VOC) emission potential of ≤25%.

2. The formulation of claim 1, comprising about 15-20 wt. % of said at least one gibberellin and about 69.5-74.9 wt. % of said at least one polyethylene glycol.

3. The formulation of claim 2, wherein the at least one gibberellin consists of $GA_3$.

4. The formulation of claim 2 wherein polyethylene glycol has a molecular weight from about 190 to 210.

5. The formulation of claim 1 comprising about 12.5 to about 15.8 $GA_3$.

6. The formulation of claim 1 wherein said at least one non-aqueous co-solvent is selected from the group consisting of ethanol, propylene glycol, hexanol, isopropanol, 3-hydoxybutyrate, 3-butyl lactate, and 2-ethylhexyl lactate.

7. The formulation of claim 1 wherein said at least one non-aqueous co-solvent have dielectric constants greater than 10 @ 20° C.

8. The formulation of claim 1 wherein said at least one non-aqueous co-solvent is selected from the group consisting of alcohols, dialkyl ketones, alkylene carbonates, alkyl esters, pyrollidones and aryl esters.

9. The formulation of claim 1 wherein said at least one surfactant is a non-ionic or anionic surfactant selected from the group consisting of carboxylates, sulfonates, natural oils, alkylamides, arylamides, alkylphenols, arylphenols, ethoxylated alcohols, polyoxygethylene, carboxylic esters, polyalkylglycol esters, anhydrosorbitols, glycol esters, carboxylic amides, monoalkanolamine, poloxyethylene fatty acid amides, polysorbates, cyclodextrins, sugar based, silicone based, polyalkylated alcohols, and alkylaryl ethoxylates.

10. The formulation of claim 1, comprising less than 5 wt. % water.

11. The formulation of claim 1, comprising about 12-20 wt. % of at least one gibberellin selected from the group consisting of $GA_3$, $GA_4$, and $GA_{4/7}$ as the only gibberellins present in said non-aqueous liquid solution.

* * * * *